United States Patent [19]
Burke et al.

[11] Patent Number: 5,824,557
[45] Date of Patent: Oct. 20, 1998

[54] METHOD FOR DETECTING AND QUANTITATING NUCLEIC ACID IMPURITIES IN BIOCHEMICAL PREPARATIONS

[75] Inventors: Thomas J. Burke, Madison; Randall E. Bolger, Oregon; Francis J. Lenoch, Madison, all of Wis.

[73] Assignee: PanVera Corporation, Madison, Wis.

[21] Appl. No.: 626,520

[22] Filed: Apr. 2, 1996

[51] Int. Cl.$^6$ .............................. C12Q 1/68; G01N 33/48
[52] U.S. Cl. .................................................. 436/94; 435/6
[58] Field of Search .................. 436/94; 435/6, 435/810

[56] References Cited

U.S. PATENT DOCUMENTS

| | | | |
|---|---|---|---|
| 4,681,859 | 7/1987 | Kramer | 436/501 |
| 4,751,190 | 6/1988 | Chiapetta et al. | 436/546 |
| 4,902,630 | 2/1990 | Bennett et al. | 436/546 |
| 4,963,658 | 10/1990 | Kung et al. | 530/406 |
| 5,393,657 | 2/1995 | Letwin et al. | 435/6 |

OTHER PUBLICATIONS

Goldman et al., Clin. Chem. 37(9), 1523–1525 (1991).
Briggs et al., Anal. Chem. 63, 850–859 (1991).

*Primary Examiner*—Kenneth R. Horlick
*Attorney, Agent, or Firm*—Mark K. Johnson

[57] ABSTRACT

A homogeneous fluorescence-based nucleic acid detection and quantitation system is provided to measure nucleic acid in protein solutions. The process relies on the intercalation of a non-fluorescent dye into a double-stranded nucleic acid helix or single-stranded nucleic acid. The dye fluoresces after intercalation and the intensity is a direct measurement of the amount of nucleic acid present in the sample.

13 Claims, 12 Drawing Sheets

Figure 3a

| ng DNA | Intensity | stdev | rel.stdev |
|---|---|---|---|
| 200 | $1.64 \times 10^6$ | $4.80 \times 10^3$ | 0.3% |
| 100 | $8.13 \times 10^5$ | $1.20 \times 10^4$ | 1.5% |
| 50 | $4.01 \times 10^5$ | $3.5 \times 10^3$ | 0.9% |
| 25 | $2.02 \times 10^5$ | $4.00 \times 10^3$ | 2.0% |
| 12.5 | $1.02 \times 10^5$ | $1.20 \times 10^3$ | 1.2% |
| 6.25 | $5.20 \times 10^4$ | 413 | 0.8% |
| 3.13 | $2.74 \times 10^4$ | 242 | 0.9% |
| 0 | $2.24 \times 10^3$ | 42 | 2.0% |

Figure 3b

| ng DNA | Intensity | stdev | rel.stdev |
|---|---|---|---|
| 25 | $1.68 \times 10^5$ | $3.98 \times 10^3$ | 2.4% |
| 12.5 | $8.5 \times 10^4$ | $1.46 \times 10^3$ | 1.7% |
| 6.25 | $4.28 \times 10^4$ | 471 | 1.1% |
| 3.13 | $2.20 \times 10^4$ | 460 | 2.1% |
| 1.56 | $1.14 \times 10^4$ | 264 | 2.3% |
| 0.781 | $5.96 \times 10^3$ | 93 | 1.6% |
| 0.391 | $3.18 \times 10^3$ | 49 | 1.6% |
| 0.195 | $1.80 \times 10^3$ | 46 | 2.6% |
| 0.098 | $1.11 \times 10^3$ | 12 | 1.0% |
| 0 | 351 | 55 | 15.7% |

Figure 3c

| slope | 8175 rfu/ng | |
|---|---|---|
| Y-Intercept | -856 | |
| Limit of Quantitation (mean of 0 + 10 x sdev) | 2680 rfu | 0.43 ng DNA |
| Limit of Detection (mean of 0 + 3 x sdev) | 2383 rfu | 0.40 ng DNA |

Figure 3d

| slope | 6700 rfu/ng | |
|---|---|---|
| Y-Intercept | 716 | |
| Limit of Quantitation (mean of 0 + 10 x sdev) | 901 rfu | 0.028 ng DNA |
| Limit of Detection (mean of 0 + 3 x sdev) | 516 rfu | -0.030 ng DNA |

Figure 3e

| trial 1 | 0.9998 |
|---------|--------|
| trial 2 | 0.9999 |
| trial 3 | 1.0000 |
| trial 4 | 0.9999 |
| trial 5 | 0.9999 |

Figure 3f

| trial 1 | 0.9999 |
|---------|--------|
| trial 2 | 1.0000 |
| trial 3 | 0.9999 |
| trial 4 | 1.0000 |
| trial 5 | 1.0000 |

Figure 4

| Compounds Tested | Fluorescence Intensity (IT) | Intensity after nuclease treatment | Percent Change after nuclease treatment |
|---|---|---|---|
| 100 ng phi-X 174 DNA | 499,000 | 6,200 | -99% |
| 100 mg Bovine Serum Albumin (BSA) | 6,200 | 2,300 | -63% |
| 15 mg Bovine Gamma Globulin (BGG) | 49,700 | 23,000 | -54% |
| 100 ng phi-X 174 DNA + 100 mg BSA | 660,000 | 2,100 | -100% |
| 100 ng phi-X 174 DNA + 15 mg BGG | 506,000 | 20,300 | -96% |

Figure 5

| DNA Source | DNA Type | Size | Florescence Intensity Relative to Equal Mass of Standard fX174 (%) |
| --- | --- | --- | --- |
| fX174 DNA RFI (Standard) | Double-stranded superhelical DNA | 5,386 bp | 100 |
| Lambda | Double-stranded circular DNA | 48,502 bp | 126 |
| E. coli | Double-stranded DNA | genomic | 103 |
| human | Double-stranded DNA | genomic | 120 |
| trp Operator | Double-stranded linear DNA | 25 bp | 25 |
| Hae III cut fX174 DNA | Double-stranded linear DNA | 490 bp ave. | 97 |
| M13mp18 | Single-stranded circular DNA | 7,250 b | 24 |
| long oligo | Single-stranded linear DNA | 125 b | 18 |
| oligo dA | Single-stranded linear DNA | 25 b | 0.3 |
| oligo dC | Single-stranded linear DNA | 25 b | 0.4 |
| oligo dT | Single-stranded linear DNA | 25 b | 7.3 |
| oligo dG | Single-stranded linear DNA | 25 b | 25 |
| oligo 1 (46% GC) | Single-stranded linear DNA | 28 b | 17 |
| oligo 2 (66% GC) | Single-stranded linear DNA | 48 b | 19 |
| RNA transcript (*luc* gene) | Single-stranded linear RNA | 1,800 b | 1.0 |
| Deoxynucleotides (equimolar A,C,G, and T) | | --- | <0.1 |

Fig. 7A

| [NaCl] mM | slope | % of control | $R^2$ |
|---|---|---|---|
| 0 | 7290 | 100% | 1.0000 |
| 20 | 4409 | 61% | 0.9999 |
| 40 | 2860 | 39% | 0.9998 |
| 80 | 1480 | 20% | 0.9998 |
| 100 | 1320 | 18% | 0.9999 |
| 150 | 846 | 12% | 0.9998 |
| 200 | 750 | 10% | 0.9999 |

Fig. 7B

| [MgCl] mM | slope | % of control | $R^2$ |
|---|---|---|---|
| 0 | 59700 | 100% | 1.0000 |
| 2 | 58900 | 99% | 0.9998 |
| 4 | 54600 | 91% | 1.0000 |
| 6 | 51300 | 86% | 0.9999 |
| 10 | 44900 | 75% | 0.9999 |
| 20 | 33200 | 56% | 0.9996 |

Fig. 7C

| % acetonitrile | slope | % of control | $R^2$ |
|---|---|---|---|
| 0 | 59700 | 100% | 1.0000 |
| 1% | 62300 | 104% | 1.0000 |
| 5% | 64800 | 109% | 1.0000 |
| 10% | 61400 | 103% | 0.9999 |

Fig. 7D

| [Urea] mM | slope | % of control | $R^2$ |
|---|---|---|---|
| 0 | 62500 | 100% | 0.9997 |
| 16 | 65300 | 104% | 0.9996 |
| 32 | 68100 | 109% | 0.9998 |
| 64 | 69500 | 111% | 0.9998 |
| 128 | 70400 | 113% | 0.9998 |
| 256 | 70200 | 112% | 0.9998 |

Fig. 7E

| % SDS | slope | % of control | $R^2$ |
|---|---|---|---|
| 0 | 54900 | 100% | 0.9998 |
| 0.001 | 60600 | 110% | 1.0000 |
| 0.005 | 67100 | 122% | 0.9999 |
| 0.01 | 63900 | 116% | 0.9999 |
| 0.02 | 50300 | 92% | 0.9992 |
| 0.05 | 29400 | 53% | 0.9996 |

Fig. 7F

| pH | slope | % of control | $R^2$ |
|---|---|---|---|
| 7 | 73000 | 100% | 1.0000 |
| 7.5 | 70500 | 97% | 0.9999 |
| 8 | 76600 | 105% | 1.0000 |
| 8.5 | 84300 | 115% | 0.9999 |

Fig. 7G

| % NP-40 | slope | % of control | $R^2$ |
|---|---|---|---|
| 0 | 6810 | 100% | 0.9999 |
| 0.05 | 7090 | 104% | 0.9999 |
| 0.1 | 7210 | 106% | 0.9999 |
| 0.2 | 7300 | 107% | 0.9999 |
| 0.4 | 7310 | 107% | 0.9999 |

Fig. 7H

| Tris-HCl [mM] | slope | % of control | $R^2$ |
|---|---|---|---|
| 50 | 3450 | 100% | 1.0000 |
| 100 | 2980 | 86% | 1.0000 |
| 250 | 1930 | 56% | 0.9998 |
| 500 | 900 | 26% | 0.9999 |
| 1000 | 180 | 5% | 0.9982 |

Figure 8

| ug BSA/ml | DNA Detected Relative to Control (ng) | DNA Standard Spiked into Sample (ng) | Percent Recovery Relative to Control |
|---|---|---|---|
| 4000 | 9.8 | 1.0 | 149.7 |
| 800 | 3.0 | 1.0 | 110.1 |
| 160 | 0.63 | 1.0 | 94.6 |
| 0 | 0.00 | 1.0 | 100 |

METHOD FOR DETECTING AND QUANTITATING NUCLEIC ACID IMPURITIES IN BIOCHEMICAL PREPARATIONS

FIELD

The field of the present invention is biological and chemical techniques for detecting nucleic acid molecules. In particular, a method for detecting nucleic acid impurities which may be part single-stranded, part double-stranded, in a mixture.

BACKGROUND

Tests for impurities and contaminants in biochemical products are critical in the development and validation of the purification process as well as in final product testing, where the test results provide on going assurance that the bioprocess remains under control. The consistency of the safety, potency, efficacy, and purity of an injectable product is ultimately the responsibility of the manufacturer and forms the basis of regulatory evaluation. Once a product is developed and approved, it is assumed that the appropriate bioprocess is in place to assure a consistent product.

The development and manufacture of drugs and biologicals have long been regulated, particularly for normally administered agents. Recent advances in measurement and purification technology have heightened awareness of potential safety hazards allowing for more stringent purity standards using new techniques.

Therapeutic biopharmaceuticals and in vitro diagnostics made by recombinant nucleic acid and monoclonal antibody based processes are typically proteins synthesized in and harvested from cultures of genetically modified cells. Thus, the starting material for the purification of each biopharmaceutical is complex, heterogeneous and potentially unsafe. Potentially dangerous impurities and contaminants include host cell molecules such as DNA. Development of appropriate analytical tools for process validation and quality control requires reliable assays for such impurities and contaminants.

Concerns about contaminating DNA as a health risk have been around since the 1950's. The primary concern with contaminating DNA is that it may contain an oncogene, or cause an oncogene to be activated, or cause a tumor inhibitory gene to be turned off.

During the 1980's, a new class of therapeutic drugs was developed and introduced to the market. These drugs are genetically recombinant human peptides or proteins and are produced by transferring human DNA to a laboratory recombinant protein expression system. These systems could be bacteria, yeast, insect cells, mammalian cell lines, or even human cell lines. The DNA that is transferred contains the genetic information which instructs the new host cell to synthesize the protein encoded by the DNA. For example, a segment of DNA could be transferred from humans to an insect cell which instructs that cell host to make the human estrogen receptor protein, or protein kinase C, or apolipoprotein E3.

Before the emergence of biotechnology, it was very unusual to purify and then detect impurities in pharmaceuticals at low parts per billion levels. Today, the FDA recommends tests for detecting contaminating DNA in the final product. The FDA tends to promote analytical goals that challenge the state-of-the-art for bioanalytical measurements. Currently, the Food and Drug Administration (FDA) has established guidelines for acceptable levels of DNA in recombinant therapeutics. Each dose must contain less that 100 picograms of total DNA which is to include DNA impurities from the host cell as well as DNA contaminants which may have been introduced during the expression and purification processes. Exceptions to these guidelines are treated on a case by case basis. Pharmaceutical companies typically establish guidelines of 10 pg total DNA/dose to exceed the FDA guidelines. DNA concentration is measured both during the purification process and at final bulk release of the purified product. In the early stages of the purification process the DNA concentrations may be several mgs/ml but will be reduced greater than a million fold throughout purification. For example, a dose of 1 mg of protein, it is necessary to detect 10 pg of DNA. On a mass basis, there is 100,000,000 times more protein than DNA. (1 mg, 1 $\mu$g, 1 ng, 10 pg). A problem is the measurement of trace impurities and contaminants in the presence of a relatively massive amount of product protein. DNA probe hybridization is an established methodology which is based upon annealing of labeled DNA probe to complementary sequences of contaminating DNA. Yet, traditional hybridization assays may be time consuming (e.g. 24–28 hour film development of 32P-labeled probe) and labor intensive (e.g. reagent handling and waste disposal). Hybridization assays only detect contaminating DNA which is complementary to the probe that is used. Other methods of quantitation include ultraviolet spectrophotometry techniques, protein binding methods and DNA amplification. Current methods to quantitate DNA during recombinant therapeutics manufacture include UV spectrophotometry, DNA hybridization, protein and antibody binding methods, and to a limited extent, DNA amplification. Each of these has both advantages and drawbacks in quantitating DNA. Some are rapid but lack sensitivity while others have the sensitivity but are slow and expensive.

Improvements in assay performance in the areas of sensitivity, precision, dynamic range, and reproducibility have allowed for improved detection and quantitation of DNA impurities.

For example, fluorescent dyes have been used to detect and quantitate DNA for decades. Many improvements have been made in the process including dyes which have higher quantum yields and therefore fluoresce more brightly. Cellular extracts typically emit more fluorescence in the ultraviolet range and less as the wavelength increases out to the red region of the spectrum. Therefore, fluorescent dyes which emit in the red spectrum tend to have less interference from naturally fluorescing cell components. Some of the newer dyes for detecting DNA only emit significant fluorescence when bound to DNA. These dyes have an advantage in that they can be added in excess to a DNA solution and not limit the sensitivity of the assay.

It is known in the field of this invention that fluorescent dyes have potential utility in detecting DNA in recombinant therapeutic drugs. However, the dye alone is not sufficient to meet FDA guidelines in detecting DNA impurities.

A prior art example of a DNA quantitation reagent is described in materials and information supplied by Molecular Probes, Inc., Eugene, Oreg.

A detection method that had been described in the early 1900's is fluorescence polarization. Fluorescence polarization assay techniques are based on the principle that a fluorescently labeled compound will emit fluorescence when excited by plane polarized light, having a degree of polarization inversely related to its rate of rotation. If the labeled molecule remains stationary throughout the excited state it will emit light in the same polarized plane; if it rotates while excited, the light emitted is in a different plane. Specifically, when a large labeled molecule is excited by plane polarized light, the emitted light remains highly polarized because the fluorophore is constrained (by its size) from rotating between light absorption and fluorescent light emission. When a smaller molecule is excited by plane polarized light, its rotation is much faster than the large molecule and the emitted light is more depolarized.

Prior art examples which utilize fluorescence polarization techniques are: U.S. Pat. No. 4,681,859 granted to Kramer, describing an immunoassay for detecting the presence of large molecular weight aqueous ligands; U.S. Pat. No. 4,751,190 granted to Chiapetta et al. and U.S. Pat. No. 4,902,630 granted to Bennett et al. describing fluorescence polarization techniques involving immunoassays with proteins.

SUMMARY

The present invention is a simple, sensitive and rapid nucleic acid detection and quantitation method that is capable of measuring nucleic acids under a wide range of conditions. The method is a fluorescence based assay to monitor nucleic acid removal, in process, during recombinant protein manufacture. The assay utilizes two standard curves which are optimized for the nucleic acid/dye ratios.

A kit is also described which can be used to measure nucleic acid in recombinant therapeutic drugs. It consists of a fluorescent dye, a highly purified buffer, a nucleic acid standard, instructions for generating standard curves over two concentration ranges, and instructions for evaluating data generated using the kit. It may contain buffer for sample preparation, if necessary.

The nucleic acid samples are diluted in a dilution buffer and the assay buffer and dye are added to the sample. Fluorescence is then measured and based on the standard curve that is generated, the concentration of nucleic acid is determined.

A process for detecting and quantitating an amount of a nucleic acid in a protein solution, comprising: measuring at least one light-emitting characteristic of a plurality of test solutions, each having a different known amount of nucleic acid and each having a nucleic acid detecting label; forming a curve based on the light-emitting characteristic measurements of step a); adding the label to a sample of the protein solution and measuring at least one light-emitting characteristic from the sample; and, comparing the light-emitting characteristic measurements of step c) with the curve and determining the amount of nucleic acid in the sample.

A process for monitoring nucleic acid removal during recombinant protein manufacture, comprising: adding a detergent to a sample of protein solution in the presence of a purified assay buffer; adding a dye that strongly emits fluorescence when intercalating with double-stranded DNA; measuring an intensity from the dye; comparing the intensity from step c) with a curve for obtaining a quantity of DNA present in the sample.

A kit for detecting and quantitating an amount of nucleic acid present in a protein sample, comprising: a receptacle containing a chemical label for detecting and quantitating and amount of nucleic acid present in a sample; a receptacle containing a purified assay buffer; a receptacle containing a nucleic acid standard for forming a curve; and, a receptacle containing a detergent for preventing nucleic acid binding to protein.

Further features and advantages of the invention will be apparent from the following detailed description when taken in conjunction with the accompanying drawings.

DESCRIPTION OF THE DRAWINGS

FIG. 3a illustrates the high range standard curve data analysis.

FIG. 3b illustrates the low range standard curve data analysis.

FIG. 3c illustrates the high range standard curve data summaries.

FIG. 3d illustrates low range standard curve data summaries.

FIG. 3e illustrates the statistical correlation R values for individual trials of the high standard curves, n=5.

FIG. 3f illustrates the statistical correlation R values for individual trials of the low standard curves, n=5.

FIG. 4 illustrates nuclease digestion of DNA standard in the presence of proteins.

FIG. 5 illustrates the specificity of the present invention for various nucleic acids.

FIG. 7 illustrates the effect of various substances on the DNA detection and quantitation method of the present invention.

FIG. 8 illustrates detection of three DNA levels in three BSA concentrations using a standard spiked sample.

DETAILED DESCRIPTION OF THE INVENTION

Figure 1:
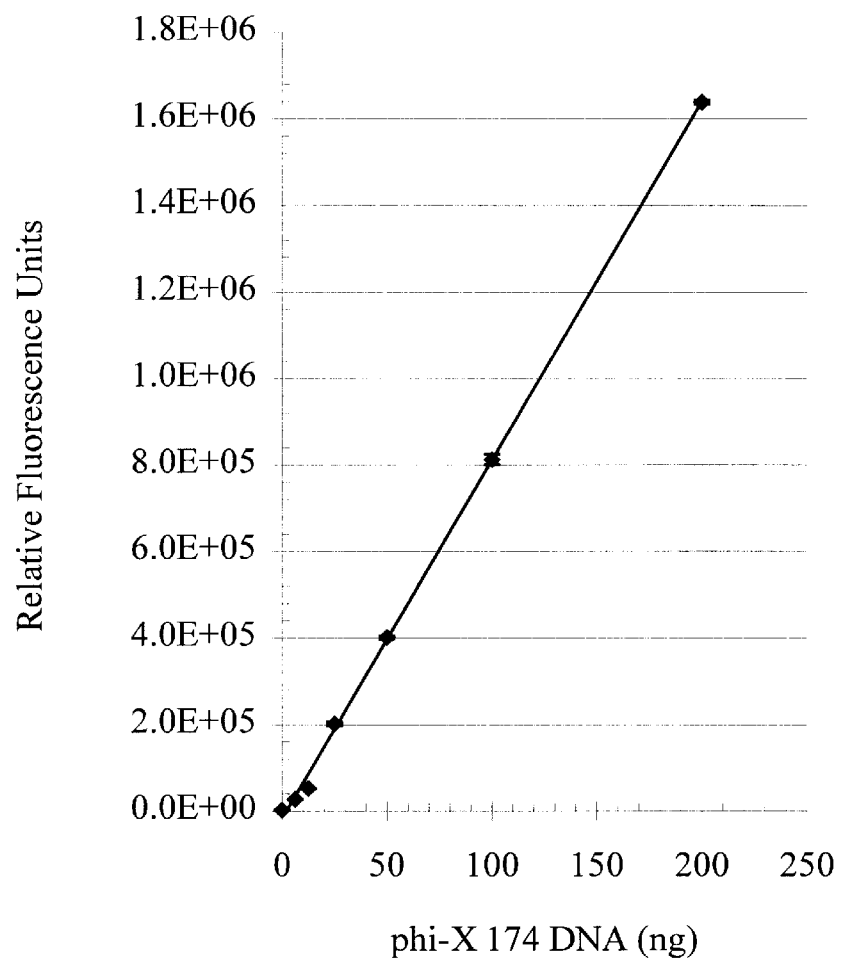
FIG. 1 illustrates a high standard curve for quantitating DNA.

The present invention is a method and kit for detecting and quantitating nucleic acid molecules. The term "nucleic acid", "polynucleotide", "oligonucleotide" are defined as multiple nucleotides attached in the form of a single or double stranded polynucleotide that can be natural; or derived synthetically, enzymatically, and by cloning methods. The use of the terms RNA and DNA may be used interchangeably in this description and include either double- or single-stranded nucleic acids. However, the preferred embodiments refer to any form of DNA.

The method and kit include the use of a light-emitting compound which is used as a label. The present invention utilizes one or more of different light-emitting characteristics for measurement. The preferred characteristics include fluorescence and polarization techniques. In a preferred embodiment, an intercalating dye is used that binds double stranded DNA and then becomes fluorescent. Fluorescence emitting compounds include any compound having appropriate fluorescence characteristics for use with the invention. One can determine whether or not a particular fluorescence emitting compound is suitable for the present invention by comparing the candidate compound with those compounds illustrated in the Examples. If the candidate compound performs a required function such that a successful detection can be obtained, similar to the compounds used in this application, the compound is suitable for use with this invention. Potential fluorescent labels for use in the invention include, for example, fluorescent dyes: acridine orange, YOYO I and PicoGreen™ (Molecular Probes, Inc.), PanVera Dye (PanVera Corp., Madison, Wis.), ethidium bromide (Sigma); each used according to manufacturer's specifications, especially regarding excitation and emission wavelengths.

The method is performed at room temperature, in the preferred embodiment. Reagents are warmed to room temperature.

Standard Curves

A curve, as used in the present invention, is at least two values obtained from measurements of light-emitting characteristics, to which a line may be plotted and used for comparison. A standard curve is generated by measuring increasing amounts of a DNA standard. The DNA standard is a known DNA, which is serially diluted into specific concentrations. A fluorescent dye is added with a light-emission characteristic which is greatly amplified when bound to double-stranded DNA. A light intensity, which in the preferred embodiment is the fluorescence intensity, value is reported at each DNA concentration. Then, a best fit line is constructed by linear regression and used to determine the DNA concentration in unknown samples. In a preferred embodiment, label nine borosilicate (PanVera Corporation, Madison, Wis.) test tubes as 1–7, 1 dye blank, and 1 buffer blank. The dye blank will contain dye solution but no DNA. It is used in the standard curve to quantitate the dye with no DNA present. The buffer blank contains no DNA or dye. It is used to blank out the background intensity in the assay buffer. 2 ml of assay buffer is added to tube 1 and 1 ml is added into all other tubes. The assay buffer is a highly purified solution containing 50 mM Tris-HCl at pH 8.0. "Highly purified" means that both the inherent DNA and fluorescence are reduced to a very low level, such that they are negligible when detecting and quantitating the amount of nucleic acid in a protein solution. The word "negligible" means the highest number one can quantitate and still meet the Limit of Detection requirements of the FDA.

We obtain the buffer by, first, purchasing the most highly purified buffer that we can find with several different manufacturing lots to check. We make up a solution and check a concentrated stock such that later dilution will provide an even more pure buffer solution. We then take the buffer and add a fluorescent dye such as PicoGreen™ and measure the fluorescence. The specification is that we measure the background fluorescence of the buffer alone. Typically this around 1000 rfu. We then add the fluorescent dye and read the intensity. If the buffer is clean the total intensity must be less than two fold over background, which would be 2000 rfu in this case. If the buffer has DNA in it, then the intensity goes up over 2000 rfu and it does not meet specifications. The buffer should have DNA in an amount less than the lowest detection limit of the low curve, about 10 pg/ml of DNA contamination, for the lot of material to be acceptable. To remove both the inherent fluorescence and the DNA, the buffer stock is passed over an ion exchange chromatography media such as Pharmacia Q Sepharose resin (or equivalent). This resin binds negatively charged molecules such as DNA very tightly. The DNA and typically other contaminants are bound to the column and the purified buffer flows through.

Some fluorescent contaminants are removed by chromatography over a cation exchange resin such as Pharmacia S Sepharose resin (or equivalent). For large molecules that contain background fluorescence, we have used membrane dialysis to allow the small fluorescent molecules to diffuse through the membrane and the large molecules were retained. We would use this method if the DNA had a lot of background fluorescence. We have used this technique to reduce the background fluorescence of BSA. Lastly, we can chemically treat protein samples to reduce fluorescence. For the BGG, we use an acetylation reaction which not only reduces fluorescence but reduces the amount of contaminating nuclease and protease activity. A suitable buffer must also have the attributes of low ionic strength along with a $K_a$ within an optimum pH range.

Serial dilutions of DNA standard (20 ng/µl) are made by adding 20 µl of the standard to tube 1, vortexing for several seconds, then removing 1 ml from tube 1 and adding it to tube 2. Continue the serial dilution 5 more times by removing 1 ml from one tube, adding it to the next, and mixing thoroughly for a total of 7 standard tubes containing 200, 100, 50, 25, 12.5, 6.25, and 3.13 ng of DNA respectively. Discard 1 ml from tube 7. All tubes should have a volume of 1 ml.

Record the fluorescence intensity value for the buffer blank for subtraction from the values obtained from each of tubes 1–7, later. Add 30 µl of the dye solution to the dye blank tube and vortex for several seconds. Record the fluorescence intensity of the tube. Similarly, add 30 µl of dye solution to tubes 1–7, vortex each time and measure the fluorescence intensity of each tube. Subtract the buffer blank intensity measurement from the intensity measurements of tubes 1–7. Construct a standard curve using linear regression (an example is illustrated in FIG. 1).

To meet the acceptable FDA limits, we utilize 2 curves with different amounts of dye added. By doing this, we obtain FDA standard limit of detection (LOD) and limit of quantitation (LOQ) values in the picogram range that have relative standard deviation values of less than 5%.

In another preferred embodiment, construct a low standard curve by making serial dilutions of the DNA standard as follows: Label eleven borosilicate tubes, 1–9, dye blank, and buffer blank. The dye blank will contain dye solution but no DNA. It is used in the standard curve to quantitate dye with no DNA present. The buffer blank contains no DNA or dye. It is used to blank out the background intensity, as described earlier. As before, dispense 2 ml buffer into tube 1 and 1 ml buffer into all other tubes.

Tubes 1–9 are used to construct a standard curve. Add 2.5 µl DNA standard (20 ng/µl) to tube 1, vortexing for several seconds, then remove 1 ml from tube 1 and add it to tube 2. Continue the serial dilution 7 more times by removing 1 ml from one tube, adding it to the next, and mixing thoroughly for a total of 9 standard tubes containing 25, 12.5, 6.25, 3.13, 1.56, 0.781, 0.390, 0.195 and 0.098 ng of DNA respectively. Discard 1 ml from tube 9. All tubes should have a volume of 1 ml.

Figure 2:
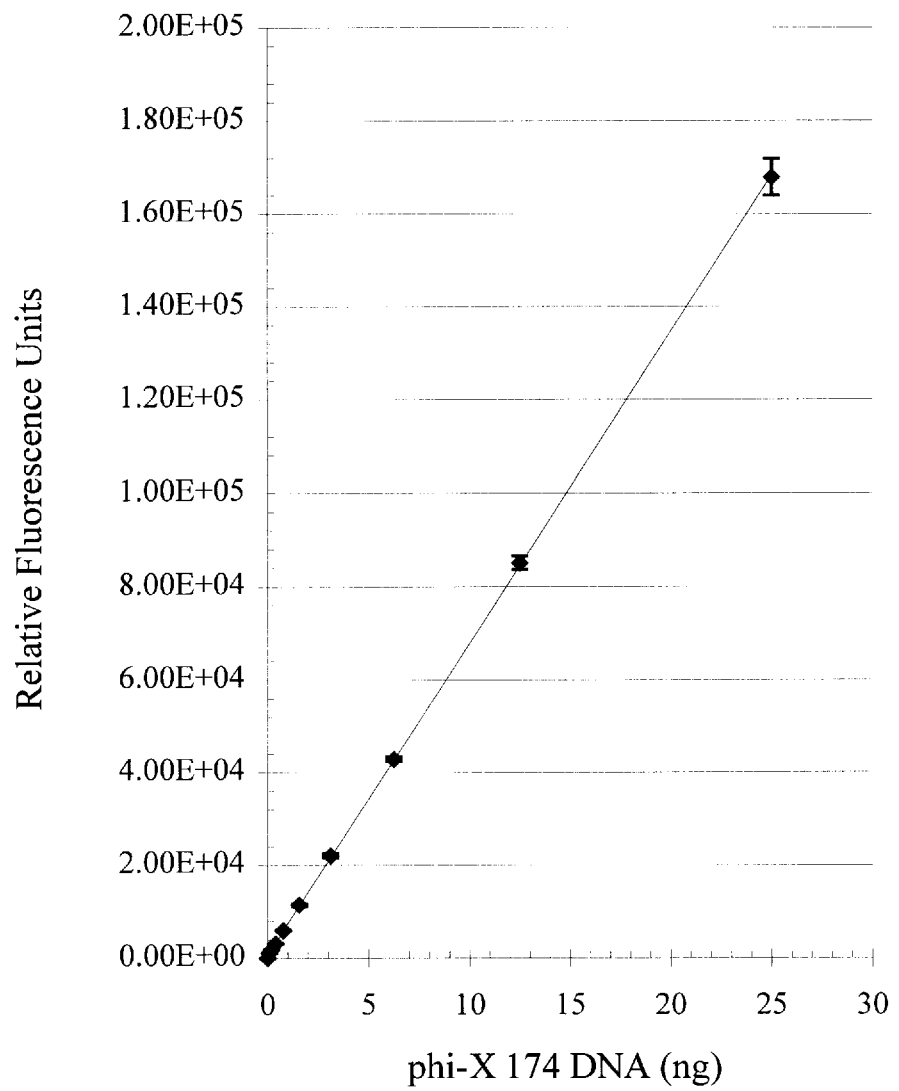
FIG. 2 illustrates a low standard curve for quantitating DNA.

Measure the fluorescence intensity of each tube 1–9 and record the results. Then record the fluorescence intensity value for the buffer blank for subtraction from the values obtained from each of tubes 1–9, later. Add 10 µl of the dye solution to the dye blank tube and vortex for several seconds. Record the fluorescence intensity of the tube. Similarly, add 10 µl of dye solution to tubes 1–9, vortex each time and measure the fluorescence intensity of each tube. Subtract the buffer blank intensity measurement from the intensity measurements of tubes 1–9. Construct a standard curve using linear regression (an example is illustrated in FIG. 2).

Preparation of Test Samples

The proper dilution for each sample will have to be determined empirically. A "sample" refers to any substance to be tested containing or presumed to contain nucleic acid.

All samples should be diluted to a final volume of 1 ml in assay buffer. Measure the fluorescence intensity background from a diluted sample. Then, add 30 μl of dye solution to the sample tube for comparison to the high standard curve, or 10 μl of dye solution for comparison to the low standard curve, remembering to vortex after adding the dye solution. Measure the fluorescence intensity and subtract the background detected earlier. The subtraction step is performed automatically when using a Beacon® Analyzer from PanVera Corporation, Madison, Wis.

Quantitation

Use the recorded sample intensity values and convert them to ng/ml using the slope and Y intercept of the best fit line formed by linear regression performed earlier from the standard curves. For example, [Intensity in sample-Y intercept]/Slope of the best fit line=DNA concentration in ng/ml. Be sure to account for the dilution of the sample. For example, if 2 μl of sample was added to 1 ml of assay buffer, there is a 500 fold dilution.

Fluorescence Polarization purification can denature DNA. These include urea treatment and elevated pH. Furthermore, PicoGreen™ (Molecular Probes, Inc., Eugene, Oreg.), a preferred DNA intercalating dye(label), does not intercalate into single-stranded DNA very well and, therefore, does not aid in efficient detection of single-stranded DNA. According to the present invention, fluorescently labeled double-stranded oligonucleotides provide a method to determine whether conditions leave DNA in a single-strand or double-strand form. Therefore, using a combination of FP with a fluorescent oligonucleotide and PicoGreen™, one can determine if DNA is partly denatured.

Fluorescence polarization is related to the time it takes a fluorescence labeled molecule to rotate through an angle of approximately 68.5 degrees: designated the correlation time. Correlation time is related to viscosity, absolute temperature and molecular volume. If viscosity and temperature are held constant, correlation time, and therefore, polarization, are directly proportional to the molecular volume. Changes in molecular volume may be due to molecular binding, dissociation, synthesis, degradation, or conformational changes of the fluorescence labeled molecule. Accordingly, when plane polarized light is passed through a solution containing a relatively high molecular weight fluorescence labeled compound, the degree of polarization of the emitted light will, in general, be greater than when plane polarized light is passed through a solution containing a relatively low molecular weight fluorescence labeled compound.

The term "Fluorescence polarization" (P) is defined as:

$$\frac{\text{Parallel Intensity} - \text{Perpendicular Intensity}}{\text{Parallel Intensity} + \text{Perpendicular Intensity}}$$

Parallel Intensity is the intensity of the emission light parallel to the excitation light plane and Perpendicular Intensity is the intensity of the emission light perpendicular to the excitation light plane. Since P is a ratio of light intensities, it is a dimension-less number and has a maximum value of 0.5 for fluorescein.

In a preferred embodiment, fluorescence polarization (the term anisotropy is closely related to polarization and is interchangeable by a simple algebraic relationship) is used to confirm that a DNA molecule is actually double-stranded rather than single-stranded. For example, if a sample is treated at pH 11 and it reads that there are 200 ng of DNA present using PicoGreen™, there may be 200 ng of double-stranded DNA, or 400 ng of DNA that is 50% double-stranded and 50% that is single-stranded. Each case would indicate similar intensities because of the binding nature of the dye. However, one can use fluorescence intensity along with polarization techniques together to determine which is correct. The fluorescence polarization methods used herein are explained fully in a patent application filed before the United States Commissioner of Patents and Trademarks, entitled: Method And Kit For Detecting Nucleic Acid Cleavage Utilizing A Covalently Attached Fluorescent Tag, Assignee: PanVera Corporation, Ser. No. 08/353,079 incorporated herein by reference. In the reference, fluorescein is attached to an end of one of the strands of the double-stranded oligonucleotide. If the DNA is double-stranded, it has a high molecular weight and therefore has a high polarization value. If the DNA is denatured and becomes single-stranded, it has a lower molecular weight and the polarization value is low. If the DNA is half single-stranded and half double-stranded, then the polarization should be intermediate between the high and low polarization values of the double-stranded and single-stranded DNA. One can look not only at the two states of the DNA but can look at all the intermediate states of 'strandedness' as well. This works because none of the methods used to denature DNA, such as base treatment, urea, or heat remove the covalently attached fluorescent tag from the oligonucleotide. These same treatments would very likely keep the PicoGreen™ from binding the DNA.

It should be clearly pointed out that in the present invention there are two different fluorescent labels. In fluorescence polarization, the oligonucleotide is covalently labeled so that the fluorescent tag does not detach with the chemicals changes that we investigated. The PicoGreen™ (and all the other intercalating dyes) bind to DNA through electrostatic and hydrophobic forces. They are typically weaker forces and can be more easily disrupted by the chemicals used herein.

To compare fluorescence polarization and an intercalating label determination (PicoGreen™, in the preferred embodiment), duplicate tubes are used. For the fluorescence polarization use a double-stranded covalently labeled oligonucleotide and titrate the pH over the listed range. If the DNA is coming apart, one detects a shift down in polarization. This indicates under which conditions the DNA is single or double or a mixture of both. For the other set of tubes, use Mbo I digested phi-X 174 DNA that is unlabeled. Add the PicoGreen™ the same range of pH samples that was used for the other DNA. As the pH is raised, one begins to observe the fluorescent signal from the PicoGreen™ go down. It is not known whether the diminished signal is from the DNA coming apart or whether the PicoGreen™ is not functional at the higher pH. The fluorescence polarization tells us that the DNA is coming apart and that is why the PicoGreen™ is not working. It is important to point out that in one set of tubes the fluorescence comes form a covalent tag and in the other set it is an intercalating dye. This is also a necessary test to determine if a protein purification method is denaturing the DNA. For example, the DNA could be spiked into a protein buffer containing 8M urea. This could denature the DNA so that it is not detectable by PicoGreen™ when it is diluted out of the urea. The fluorescence polarization method will indicate whether the DNA is single- or double-stranded and whether or not one should expect the PicoGreen™ to work.

Detergent

In another preferred embodiment, a detergent is used to enhance the quantitation method. It is known that nucleic acid has a tendency to bind to proteins. Therefore, in a protein solution that is to be tested for amounts of nucleic acid impurities, the protein could interfere with DNA measurements by competing with a dye for binding. However, the present invention provides an answer to this problem by introducing a detergent to the sample solution, which prevents DNA from binding to proteins. By interfering with the chemicals forces which bind the protein to the DNA, such as electrostatic, hydrophobic, and hydrophilic attractions. The proteins coat the outside of the DNA and prevent the PicoGreen™ from intercalating into the DNA double helix.

In the preferred embodiment, when the samples are pretreated with SDS, an ionic detergent, the method has significantly improved performance. SDS is one example of a detergent that is useful with the present invention. However, many detergents will perform well and may be substituted for SDS in the method. A suitable detergent will be able to prevent nucleic acid binding to proteins. Particularly suitable detergents are: 1) a class called alky sulfates including LDS; 2) a class called the bile acids which includes the cholate detergents such as sodium deoxycholate; 3) a class called the quaternary ammonium class including a detergent called CTAB.

If one wishes to determine whether or not a particular detergent is suitable for the present invention, one can test whether the detergent has: 1) the ability to prevent nucleic acid binding to proteins; 2) does not have inherent fluorescence that interferes with the intercalating dye fluorescence; 3) separates proteins or other contaminants from DNA and 4) does not interfere with the intercalating dye either in high concentration or when diluted out. A candidate detergent can be tested for appropriate characteristics by exposing it to a solution of proteins in the presence of nucleic acid, inserting a dye, and measuring the results. The results should be compared to results from a solution without inserting the candidate to determine its usefulness. If the candidate performs by preventing nucleic acid binding to the proteins, it is considered suitable to the present invention.

Quantitation Kit

A kit is formed according to the process and methods provided. In the preferred embodiment, the kit contains the following:

a receptacle containing an assay buffer of 50 mM Tris-HCl, pH 8.0;
  a receptacle containing PanVera Dye;
  a receptacle containing DNA standard of 20 ng/$\mu$l of $\phi$X174
  RF1 DNA in assay buffer.

In another preferred embodiment, the items listed, plus one or more of the following:

a receptacle containing SDS detergent;
  a receptacle containing a known amount of double-stranded DNA covalently bound to a polarization-readable label;
  pipettes, test tubes, test tube racks, vortexer; and,
  instructions for use.

By the term "instructions for use," it is meant a tangible expression describing the reagent concentration for at least one assay method, parameters such as the relative amount of reagent and sample to be admixed, maintenance time periods for reagent/sample admixtures, temperature, buffer conditions and the like.

Definitions from FDA's Validation of Compendial Methods (incorporated herein by reference)

Precision

Precision is a measure of assay reproducibility. Measure (evaluate) the variation in homogeneous samples by performing several independent analysis and determining mean and relative standard deviation. A minimum of six replicates with a relative standard deviation (RSD) and not more than (NMT) 2% is acceptable for most methods.

Accuracy

Accuracy measures the compatibility of the assay value with a true or absolute value or standard. For example, demonstrate the ability of the assay to reviver a know amount of analyte and express the result as a percentage. Replicates of 6 and recoveries or accuracy's of 60–100% are acceptable for concentration below 100 ppb; recoveries of 80–100% are acceptable for concentrations above 100 ppb.

Limit of Detection

Limits of detection specify the lowest concentration of a sample that can be detected within the method (not necessarily the lowest amount that can be quantitated). When the assay is routinely performed test samples should contain 2–3 time the minimum amount capable of detection.

Limit of Quantitation

Limits of quantitation specify the lowest concentration of a sample that can be quantified with an acceptable degree of precision. For instrument methods determine the standard deviation (SD) of a series of blanks, and multiply the SD by 10 for an estimate of the limit of quantitation. Confirm this with samples prepared with this concentration.

Specificity

Related to selectivity and interference. Specificity is a measure of the assay's sensitivity to impurities, related chemical compounds and degradation products of product excipients. They measure the degree of interference.

Linearity and Range

Linearity demonstrates that the method can elicit results that are mathematically related to the concentration of the analyte in the sample. Linearity is usually demonstrated over a defined range of analyte concentration. The slope of the regression line and its variance (R) provide a mathematical measure of linearity; the y intercept is a measure of potential assay bias. Range is validated by demonstrating accuracy and precision at it extremes. If the assay is not linear (log/log or log/linear) demonstrate these relationships as well.

Correlation

If the assay replaces an existing assay or is used to support another assay which measures a directly related characteristic, it may be appropriate to evaluate the correlation between assays. Such an evaluation requires that identical samples be tested several times by both methods. Ruggedness (Robustness) The ruggedness of an assay is a measure of its reproducibility in the face of variations such as analysts, different instrumentation, lots of reagents or elapsed assay times. To test ruggedness, compare the reproducibility of the sassy when challenged under extreme conditions with the precision of the assay under normal conditions. For example, the evaluate the ruggedness of the assay when performed by different technicians, have four analysts perform the assay per day for three days with identical samples and evaluate precision.

EXAMPLES

A preferred embodiment uses a proprietary dye PanVera Dye, $\phi$x174 RF1 DNA from the phage phi X 174 as a standard, and Tris-HCl buffer. As the dye intercalates into the DNA helix, it emits fluorescence (530 nm) directly proportional to the amount of DNA present. This method was tested in the presence of several matrix components and proteins to see if they induce or diminish dye fluorescence. This method was compared to a spike and recovery experiment for detecting DNA spiked into protein solutions. All fluorescence measurements were performed using a Beacon® Analyzer or Beacon 2000 Analyzer(PanVera Corporation) with bandpass filters at 485 nm excitation and 530 nm emission. Fluorescence was reported in relative fluorescence units (rfu) and is dependent on the photomultiplier tube (PMT) voltage setting. The PMT voltage was kept constant for each individual experiment but may have been altered between experiments. Therefore, sample intensities can be compared within an experiment but it is not valid to compare them between experiments. This variation in PMT voltage allowed for a larger dynamic range of the instrument in measuring fluorescence intensity.

It is important the DNA standard also be made up in a buffer which has very low fluorescence background. If there is light coming from the buffer containing the DNA, it will give artificially high numbers. The water that goes into making up these buffers is highly purified through 4 cartridges and then sterile filtered to remove bacteria. Bacteria can be a source of DNA contamination. The SDS that is used also has to be of low fluorescence background and low DNA content.

Standard Curve Analysis

The fluorescent dye solution was added to DNA in Tris-HCl buffer, mixed, and the fluorescence intensity was measured. The two blanks defined in the assay were the buffer blank (Tris-HCl buffer, 50 mM, pH 8.0) and the sample blank (buffer blank with fluorescent dye containing no DNA). The sample blank intensity was used to establish the sensitivity limits in the assay. DNA quantitation was performed using two standard curves (FIGS. 1 and 2), each optimized for dye/DNA concentration. The high standard curve was linear from 3.13 ng to 200 ng DNA with a correlation coefficient R value of 1.0000 and an LOQ (limit of quantitation) of 0.033 ng DNA. The low standard curve was linear from 0.098 ng to 25 ng DNA with a typical R value of 1.0000 and an LOQ of 0.024 ng DNA. A correlation coefficient of 1.0000 is typical for these standard curves. The LOQ was calculated by adding the mean intensity of the sample blank and 10 times the standard deviation of the sample blank. For example, for the high-standard curve, the mean blank intensity (n=5) was 2,240 rfu with a standard deviation of 42 rfu. The LOQ intensity was 2,240+(10×42) =2,680 rfu. On the standard curve, this extrapolated to DNA concentration of 0.43 ng/ml. Similarly, the LOD was calculated using the mean blank intensity plus three standard deviations.

To demonstrate the precision in the standard curves, five low-range standard curves and five high-range standard curves were generated using the DNA method. The mean, standard deviation and relative standard deviation (RSD) from the five high-range and five low-range trials are shown in FIGS. 3a and 3b.

NA Standard was serially diluted in 8 glass tubes from 150 to 1.17 ng in 1 ml of Assay Buffer. A separate dilution series was performed in Assay Buffer containing 0, 20, 40, 80, 100, 150, and 200 mM NaCl. 30 µl of the fluorescent dye was added to each tube and the fluorescence intensity in each tube was measured. The graph is a plot of fluorescence intensity versus the concentration of the DNA Standard at the various NaCl concentrations. The best fit line generated using the method of least squares is also shown for each standard curve. This data shows the trend that increasing NaCl concentration decreases the sensitivity of the assay.

The slope, Y-intercept, and correlation coefficient for the "best fit" line using the method of least squares are also shown in FIGS. 3c and d. The statistical correlation R values for individual trials of the high and low standard curves, n=5 are shown in FIGS. 3e and f, respectively. The RSD values for each DNA sample measurement were $\leq 2.0\%$, while the high and low sample blanks have RSD values of 2.0% and 15.7%, respectively. A standard curve was developed for single-stranded DNA using the circular phage M13mp18. Five standard curves were generated with 9 DNA concentrations from 390 pg/ml to 100 ng/ml. The relative standard deviations were less than 3.2% and the mean R value was 0.9999.

Nuclease Degradation

Nuclease digestion of the DNA reduced dye intercalation and therefore caused a proportional decrease in fluorescence intensity. The DNA concentration (100 ng/ml) was measured alone or in 100 µg/ml bovine serum albumin (BSA) or 15 µg/ml bovine gamma globulin (BGG) at 10 minutes, 1 hour, 4 hours and 72 hours. Three duplicate tubes were treated the same except that bovine deoxyribonuclease I (DNase I) and phosphodiesterase I (PDE I) were added to digest the DNA into short oligonucleotides and mononucleotides. The sample blank intensity was subtracted from each of the reported sample intensities. The fluorescence intensity in the 100 ng φx174 DNA solution was reduced 99% after nuclease treatment for 72 hours (499,000–6,200 rfu) (shown in FIG. 4). The intensities of the BSA and BGG solutions were 6,200 rfu and 49,770 rfu higher than the sample blank intensity, 9,800 rfu. The fluorescence intensity due to the spiked DNA decreased more than 50% when treated with the nuclease mixture.

In a separate control experiment to show that the decrease in fluorescent signal was due to deoxyribonuclease degradation and not dye/protein interactions, ribonuclease A and ribonuclease T1 were added to DNA samples. While the DNase I and PDE enzymes digested the DNA to near completion and reduced the fluorescence intensity significantly, the RNase had little effect on the DNA degradation and fluorescence intensity (less than 5% change in intensity relative to the control).

Specificity

Various nucleic acids were tested using the quantitation method described to determine the specificity of the assay (illustrated in FIG. 5). In these experiments, 100 ng of each nucleic acid or nucleotide sample was quantitated using the fluorescent assay and the intensity was compared to the intensity from 100 ng of the φX174 standard DNA. The nucleic acids tested were of various sizes, RNA or DNA, single-stranded or double-stranded, circular, linear, or superhelical. Material was tested from bacterial, viral, and mammalian sources. Purified nucleic acids were quantitated first by ultraviolet absorbance at 260 nm. The fluorescent intensity of lambda phage, $E.$ $coli$, human, and a synthetic 25 basepair(bp) oligonucleotide were 126%, 103%, and 120% respectively. φX174 DNA (5386 bp) was digested with the restriction enzyme Hae III to produce 11 fragments with an average size of 490 bp and a range of 73 bp to 1353 bp. The fluorescence intensity of the 100 ng of digested DNA was 97% of the undigested control DNA.

Single-stranded DNA samples, including oligonucleotide homopolymers, were also tested for specificity in the present invention (FIG. 5). The intensity of the single-stranded oligonucleotides ranged from 0.3 to 19% of the control. An M13mp18 sample emitted at 24% of intensity for an equivalent amount of double-stranded standard. The standard curve for single stranded DNA showed that the sensitivity was lower but the linearity of assay was equal (R=0.9999). An 1,800 base synthetic RNA transcript showed <1% relative to an equal mass of control DNA.

Matrix Effects on Sensitivity and Linearity

Figure 6:
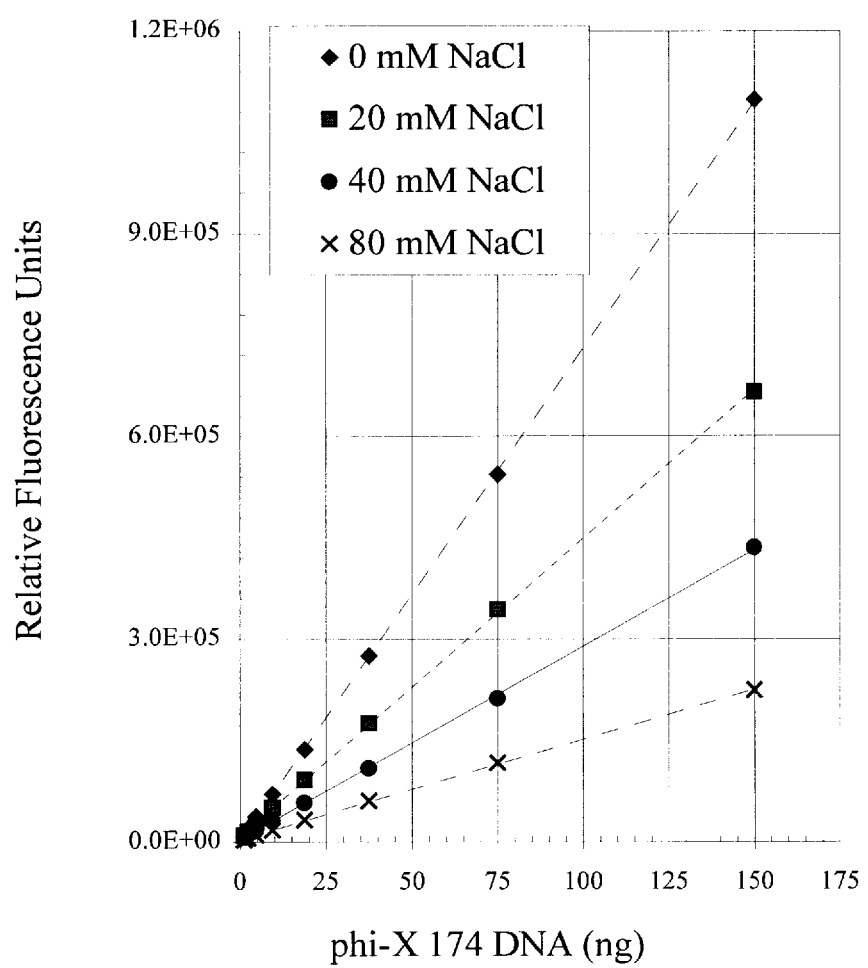
FIG. 6 illustrates the effect of NaCl on fluorescent dye used in the present invention.

The sensitivity of the DNA quantitation assay to common matrix components such as salts, detergents, buffers, solvents, and denaturants was tested. Standard curves were generated in the presence of several different concentrations of each component to determine the effect on the assay. The NaCl matrix experiment was representative of how the other experiments were performed (FIGS. 6 and 7). Seven DNA standard curves ranging from 780 pg to 50 ng were generated in the presence of 0, 20, 40, 80, 100, 150, and 200 mM NaCl. The slope of the standard curve decreased 90% with the addition of 200 mM NaCl. However, the linearity of the assay does not change (R=0.9999). The same type of experiments were performed with magnesium chloride, acetonitrile, urea, SDS, pH, NP-40, and Tris-HCl.

Effect Of Various Potentially Inhibitory Compounds

Standard φX174 DNA was serially diluted from 25 to 0.78 ng in 1 ml volumes of Assay Buffer. The dilution series was repeated with the addition of a range of concentrations of various potentially inhibitory compounds. 10 $\mu$l of the fluorescent dye was added to each tube and the fluorescence was measured on a Beacon® Analyzer. A best fit line using the method of least squares was generated for each dilution series and reported in the tables below. The slope for each dilution series containing the added compounds was compared to the slope for the dilution series containing no added compounds by reporting the slope as a percent of the control slope. The R value (correlation coefficient) is also reported for each series in order to demonstrate that although the presence of some matrix components may reduce the sensitivity of the assay, the linearity does not change significantly. The data is summarized in FIG. 7.

Correlation With Spike and Recovery Method

The present invention was used to detect three DNA levels in three BSA concentrations (4,000 $\mu$g/ml and 800 $\mu$g/ml and 40 $\mu$g/ml) and measured. The samples were measured directly using our method. The results are shown in FIG. 8.

BSA was diluted fivefold in assay buffer of the present invention. A fluorescent dye was added to the buffered protein solution and the intensity was measured and identified as the DNA detected relative to the control (FIG. 8). The intensity could actually be due to either DNA that was an impurity or contaminant in the protein or interactions between the protein and the dye which caused it to emit fluorescence. Standard DNA ( 1 ng) was then spiked into each sample and the intensity was measured again. The amount of DNA recovered in the assay was determined from a standard curve and expressed as a percent of the spiked DNA in the control. The 1 ng DNA spiked into the 4000 $\mu$g BSA sample represents a 250 ppb concentration.

Procedures, Materials and Results

Experiments were performed in which the dye was added to purified BSA or BGG spiked with standard DNA. The observed fluorescence was from the dye intercalating into the DNA helix since the nuclease digestion of the DNA to mononucleotides reduced the fluorescence greater than 95%. It is likely that during and after protein purification, DNA could be partially denatured and/or degraded. The DNA standard in the assay is a well characterized supercoiled, circular, double-stranded molecule which is 44.8% GC. We found that for long cellular and viral DNA samples, equivalent amounts of DNA emitted fluorescence values within 20% of the standard. For a short (25 bp) oligonucleotide, the fluorescence was reduced to 25% of the control DNA. The total intensity of 100 ng of the Hae III digested φ174 DNA was 97% of the undigested DNA showing that as long DNA fragments are shortened during purification, they are detected with very similar efficiency.

The standard curve range for the fluorescence system is homogenous and takes minutes to quantitate DNA whereas other systems take hours. The present invention is designed to perform directly in protein solutions, avoiding costly sample preparation methods.

Fluorescence Polarization

Make a triple buffer—500 ml:

10 ml of 1M Tris;

10 ml of 1M phosphate;

100 ml of 1M carbonate, 0.5M NaCl;

$H_2O$ to 500 ml, then adjust pH to about 5.0;

add buffer to 10, 50 ml beakers and adjust the pH in each to: 12.0, 11.6, 11.2, 10.8, 10.4 10.0, 9.5, 9.0, 8.5, 8.0 respectively;

add 20 $\mu$l of fluorescein end-labeled, double-stranded oligonucleotide to each tube and record the polarization level on a Beacon® Analyzer.

Figure 9:
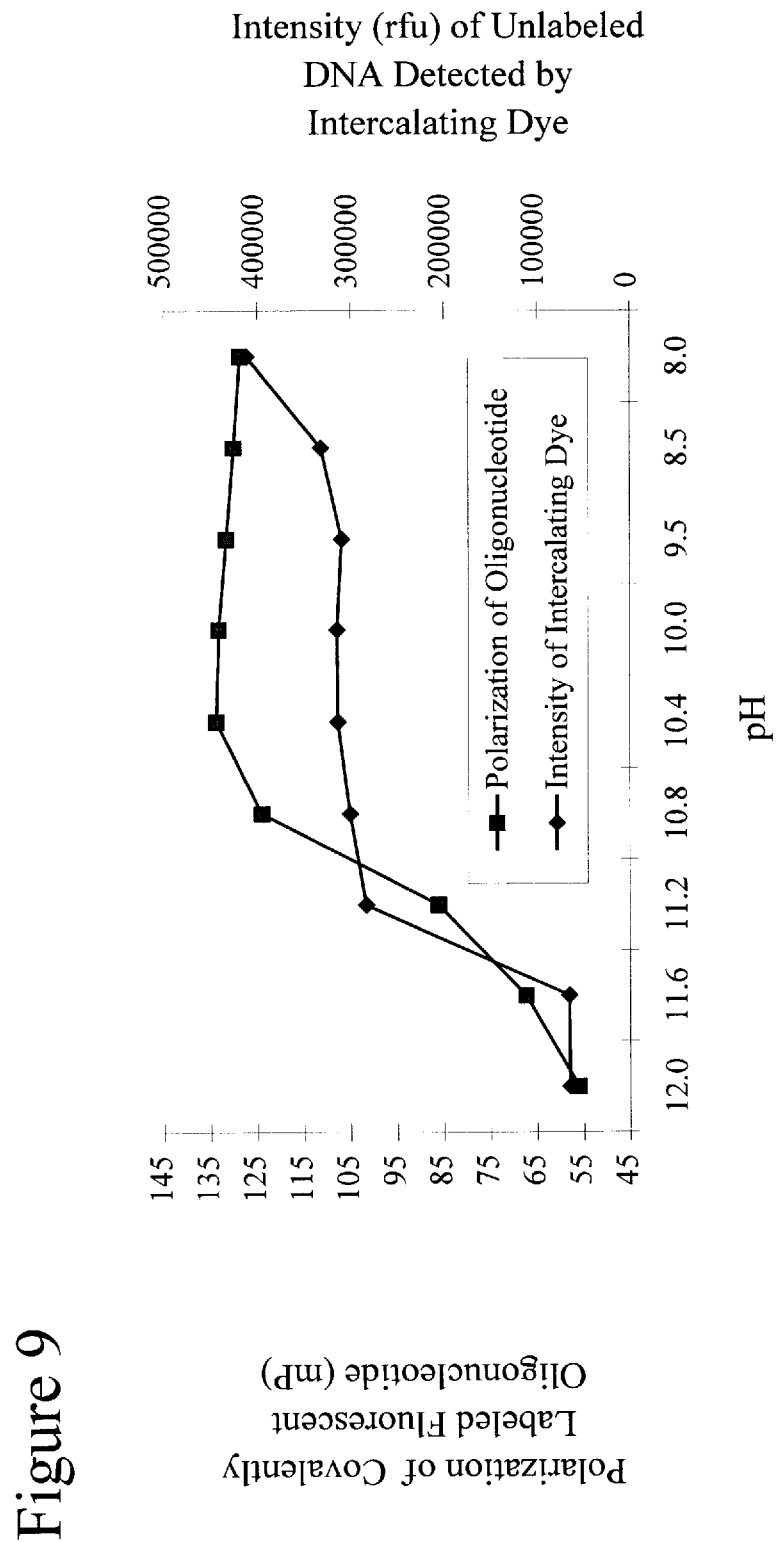
FIG. 9 illustrates measuring the pH effect on DNA detection by using both fluorescent dye intercalation and fluorescence polarization.

PicoGreen™ determination of DNA:

add 11 $\mu$l Mbo I phi-X 174 DNA at 1.8 ng/$\mu$l to 190 $\mu$l of each of 10 tubes at the different pH values; Mbo I digested phiX 174 DNA to 190 $\mu$l of duplicate 10 tubes containing the buffers adjusted to different pH. (Note that there are duplicates and the fluorescence from the first set comes from covalent tag and the fluorescence from the second set come from the intercalating PicoGreen™)

let sit for 20 minutes;

add 10 $\mu$l PicoGreen™ to 10 tubes of 1 ml buffer;

add 10 $\mu$l of each DNA sample and record fluorescence intensity, immediately;

prepare low curve graph (shown in FIG. 9).

The results show the correlation between the intensity and polarization. Plot pH value versus intensity of the PicoGreen™ and plot pH versus polarization value for the fluorescently tagged oligonucleotide. The polarization indicates that the DNA comes apart in the range that the PicoGreen™ is no longer intercalating and fluorescing.

Treatment With SDS

Treat a DNA/protein sample with a high concentration of SDS and then dilute out the SDS and use PicoGreen™ to measure the DNA. We used human recombinant estrogen receptor expressed in insect cell culture using baculovirus. We had three pools of material: whole cells, a nuclear fraction, and a cytoplasmic fraction (extracts). We used SDS and heat to determine if pretreatment gave better results.

Prepare the buffer:

10 ml of 50 mM Tris-HCl, pH 8.0;

|    |          | 10% SDS   | $H_2O$    |
| -- | -------- | --------- | --------- |
|    | Crude whole cells |   |   |
| 1. | 100 $\mu$l | 100 $\mu$l | 800 $\mu$l |
| 2. | 100 $\mu$l |           | 900 $\mu$l |
| 3. | 100 $\mu$l | 100 $\mu$l | 800 $\mu$l |
| 4. | 100 $\mu$l |           | 900 $\mu$l |
|    | Cytosol  |           |           |
| 5. | 100 $\mu$l | 100 $\mu$l | 800 $\mu$l |
| 6. | 100 $\mu$l |           | 900 $\mu$l |
| 7. | 100 $\mu$l | 100 $\mu$l | 800 $\mu$l |
| 8. | 100 $\mu$l |           | 900 $\mu$l |

-continued

Figure 10:
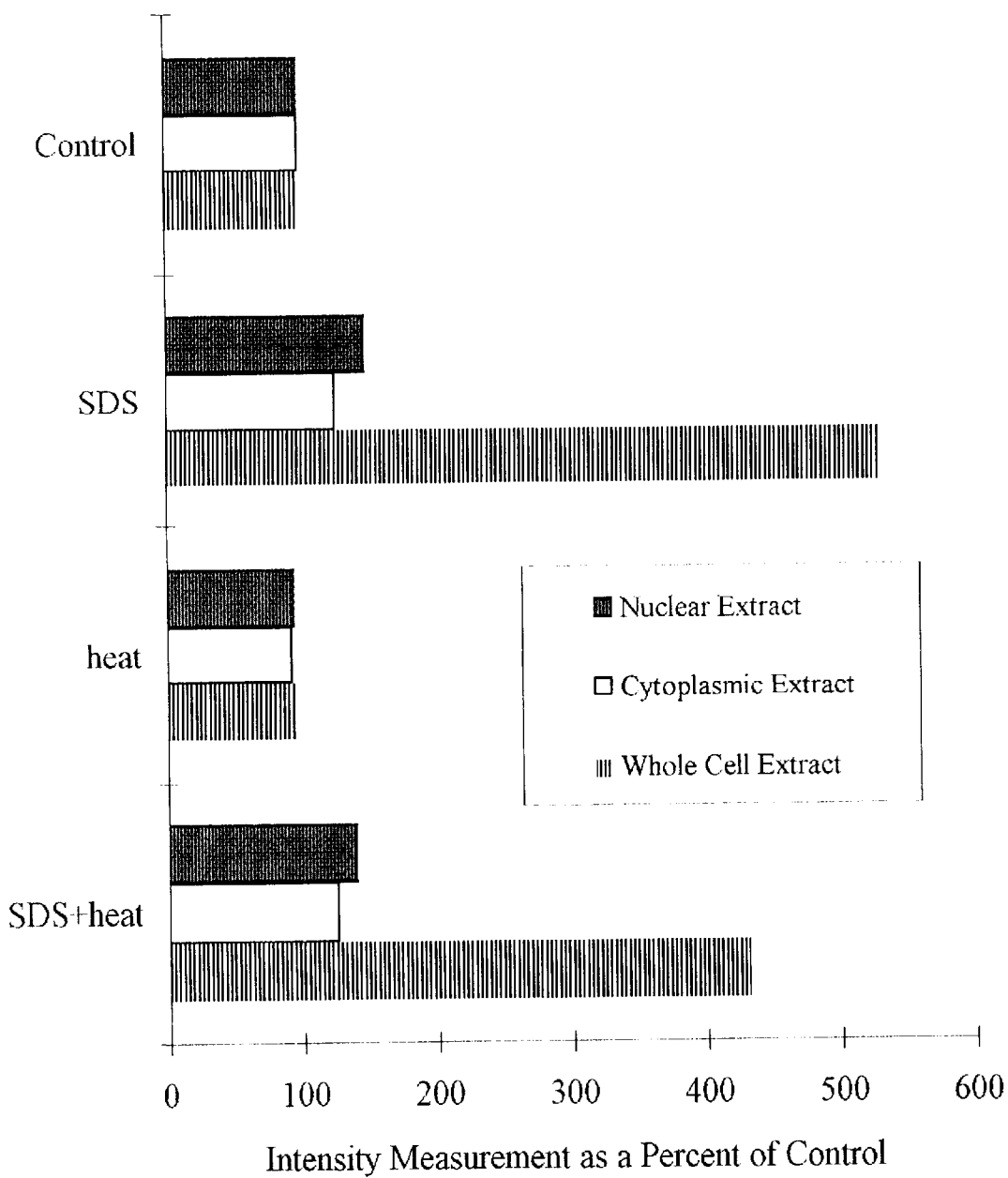
FIG. 10 illustrates the effect of SDS on fluorescence intensity emitted by the intercalating dye testing 3 cellular substances.

|     | 10% SDS | H$_2$O |
| --- | --- | --- |
|     | Nuclear extract | |
| 9.  | 100 µl | 100 µl | 800 µl |
| 10. | 100 µl |        | 900 µl |
| 11. | 100 µl | 100 µl | 800 µl |
| 12. | 100 µl |        | 900 µl | heat tubes 1,2,5,6,9,10 to 650° C., for about 20 minutes; the rest of the tubes remain at room temperature;

dilute all tubes 1:100 in assay buffer 10 µl to 1 ml into tubes 13–24;

add 100 µl of each to 900 µl buffer and 30 µl PicoGreen™ and record fluorescence intensity on high standard curve as shown previously;

results are shown in FIG. 10.

In an example of using fluorescence polarization to monitor detergents interrupting protein DNA interactions, we measure the polarization of the labeled double-stranded oligonucleotide. We then add the DNA binding protein and see the polarization value go up because the DNA/protein complex has a higher molecular weight. If we added SDS to this complex, it interacts with the protein and keeps it from binding to the DNA. Therefore, the polarization goes back down. This polarization experiment shows directly that we can disrupt protein/DNA binding with detergents. This is our rational for pre-treating samples with SDS. The detergent disrupts the protein DNA interactions and frees the DNA up to bind to the PicoGreen™. We have to make sure that the SDS is at high enough concentration to disrupt protein/DNA binding but is then diluted out far enough so that it does not interfere significantly with the PicoGreen™ binding.

Additional Information

In a kit:

for superior DNA removal it is desirable to autoclave pipettes, even disposable pipettes, eliminating significant DNA contamination.

the limit of quantitation must not be greater that 0.43 ng/ml for the high standard curve.

the limit of quantitation must not greater that 0.028 ng/ml for the low standard curve.

the relative standard deviation values for the standard curve sample must be less than 3% to 5%.

the process must detect single-stranded DNA with secondary structure by giving a standard curve with R value>0.999.

the process must detect DNA in the presence of matrix components so that the linearity of the standard curve is>0.999 e.g. NaCl, acetonitrile, SDS etc. The significance of the results of potentially inhibitory substance is that even thought the LOD and LOQ are lower, the linearity (R value) is still>0.999.

Sources of Materials

In the experiments and methods: lyophilized bovine pancreatic DNase I, human DNA and *E. coli* DNA were from Sigma, St. Louis, Mo.; phosphodiesterase I from Crot. Adamanteus was from Pharmacia, Milwaukee, Wis.; φX174 RFI double stranded DNA,M13mp18 single-stranded DNA, and RNA transcript, Tris-HCl, MgCl$_2$, NaCl, and SDS were from PanVera Corporation, Madison, Wis.; Lambda DNA was from Promega Corp., Madison, Wis.; synthetic oligonucleotides were from Eppendorf, Madison, Wis.; deoxynucleotides were from TaKaRa Shuzo, Japan; NP-40 was from Pierce, Rockford, Ill.; the urea and acetonitrile were from Fisher Scientific, Fair Lawn, N.J.

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

What is claimed is:

1. A process for detecting and quantitating an amount of a nucleic acid in a protein solution, comprising:
    a) measuring at least one light-emitting characteristic of a plurality of test solutions, each having a different known amount of nucleic acid and each having a nucleic acid detecting label;
    b) forming a curve based on the light-emitting characteristic measurements of step a);
    c) adding the label to a sample of the protein solution having a detergent and measuring at least one light-emitting characteristic from the sample; and,
    d) comparing the light-emitting characteristic measurements of step c) with the curve and determining the amount of nucleic acid in the sample.

2. The process of claim 1 wherein the label is a light-emitting compound.

3. The process of claim 2 wherein the light-emitting compound intercalates with nucleic acid and emits light more strongly when intercalating with double-stranded nucleic acid and less strongly when intercalating with single-stranded nucleic acid.

4. The process of claim 3 wherein the light-emitting compound is a fluorescence-emitting dye which is selected from the group consisting of PicoGreen™, acridine orange, YOYO I, PanVera Dye and ethidium bromide.

5. The process of claim 1 wherein the light-emitting characteristic is selected from the group consisting of intensity and polarization.

6. The process of claim 1 wherein the detergent is selected from the group consisting of SDS, alky sulfates, bile acids and quaternary ammonium detergents.

7. The process of claim 1 wherein the nucleic acid is selected from the group consisting of DNA and RNA.

8. The process of claim 1 further comprising detecting and quantitating an amount of a nucleic acid in a protein solution for monitoring nucleic acid removal of a recombinant protein manufacture.

9. A process for monitoring nucleic acid removal during recombinant protein manufacture, comprising:
    a) adding a detergent to a sample of protein solution in the presence of a purified assay buffer;
    b) adding a dye that strongly emits fluorescence when intercalating with double-stranded DNA;
    c) measuring an intensity from the dye;
    d) comparing the intensity from step c) with a curve for obtaining a quantity of DNA present in the sample.

10. The process of claim 9 wherein the detergent is selected from the group consisting of SDS, alky sulfates, bile acids and quaternary ammonium detergents.

11. The process of claim 1 further comprising the assay buffer having an amount of inherent fluorescence and DNA material that is negligible when obtaining the quantity of DNA present in the sample.

12. A kit for detecting and quantitating an amount of nucleic acid present in a protein sample, comprising:
    a) a receptacle containing a chemical label for detecting and quantitating an amount of nucleic acid present in a sample;

b) a receptacle containing a purified assay buffer;

c) a receptacle containing a nucleic acid standard for forming a curve; and, d) a receptacle containing a detergent for preventing nucleic acid binding to protein.

13. The kit of claim 12 further comprising a receptacle containing a known amount of double-stranded nucleic acid covalently bound to a polarizationly readable label.

* * * * *